United States Patent
Serrano Carmona (10) Patent No.: US 10,625,072 B2
(45) Date of Patent: Apr. 21, 2020

(54) ELECTRICAL STIMULATION METHODS WITH OPTICAL OBSERVATION AND DEVICES THEREFOR

(71) Applicant: Boston Scientific Neuromodulation Corporation, Valencia, CA (US)

(72) Inventor: Raul Enrique Serrano Carmona, Los Angeles, CA (US)

(73) Assignee: BOSTON SCIENTIFIC NEUROMODULATION CORPORATION, Valencia, CA (US)

(*) Notice: Subject to any disclaimer, the term of this patent is extended or adjusted under 35 U.S.C. 154(b) by 272 days.

(21) Appl. No.: 15/789,576

(22) Filed: Oct. 20, 2017

(65) Prior Publication Data

US 2018/0110971 A1   Apr. 26, 2018

Related U.S. Application Data (60) Provisional application No. 62/411,203, filed on Oct. 21, 2016.

(51) Int. Cl.
*A61N 1/05* (2006.01)
*A61N 1/372* (2006.01)
(Continued)

(52) U.S. Cl.
CPC .............. *A61N 1/05* (2013.01); *A61B 5/0071* (2013.01); *A61B 5/0084* (2013.01);
(Continued)

(58) Field of Classification Search
None
See application file for complete search history.

(56) References Cited

U.S. PATENT DOCUMENTS

| 5,076,270 A | 12/1991 | Stutz, Jr. |
| 5,437,193 A | 8/1995 | Schleitweiler et al. |

(Continued)

FOREIGN PATENT DOCUMENTS

| WO | 2011/150430 | 12/2011 |
| WO | 2012/103543 | 8/2012 |
| WO | 2014143387 | 9/2014 |

OTHER PUBLICATIONS

Vallejo, Ricardo, Kerry Bradley, and Leonardo Kapural. "Spinal cord stimulation in chronic pain: Mode of action." Spine 42 (2017): S53-S60.

(Continued)

*Primary Examiner* — Brian T Gedeon
(74) *Attorney, Agent, or Firm* — Lowe Graham Jones PLLC; Bruce E. Black (57) ABSTRACT

A method of monitoring electrical stimulation includes electrically stimulating tissue of a patient using at least one electrode of an implanted electrical stimulation lead. A distal portion of the electrical stimulation lead is disposed adjacent to the tissue of the patient to be stimulated. The electrical stimulation lead includes the at least one electrode and at least one light receiver disposed along the distal portion of the electrical stimulation lead. The method also includes receiving light from the tissue at the at least one light receiver of the lead. Other methods include emitting light from the lead to induce the emission of light or electrical signals from the tissue which are then received by the lead.

20 Claims, 9 Drawing Sheets

(51) Int. Cl.
  *A61B 5/00* (2006.01)
  *A61N 1/36* (2006.01)
  *A61B 5/04* (2006.01)
(52) U.S. Cl.
  CPC ...... *A61N 1/36139* (2013.01); *A61B 5/04001* (2013.01); *A61N 1/37235* (2013.01)

(56) References Cited

U.S. PATENT DOCUMENTS

| | | |
|---|---|---|
| 5,445,608 A | 8/1995 | Chen et al. |
| 5,556,421 A | 9/1996 | Prutchi et al. |
| 6,175,710 B1 | 1/2001 | Kamaji et al. |
| 6,181,969 B1 | 1/2001 | Gord |
| 6,224,450 B1 | 5/2001 | Norton |
| 6,271,094 B1 | 8/2001 | Boyd et al. |
| 6,295,944 B1 | 10/2001 | Lovett |
| 6,364,276 B1 | 4/2002 | Lin et al. |
| 6,391,985 B1 | 5/2002 | Goode et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 6,988,001 B2 | 1/2006 | Greatbatch et al. |
| 6,993,384 B2 | 1/2006 | Bradley et al. |
| 7,190,993 B2 | 3/2007 | Sharma et al. |
| 7,244,150 B1 | 7/2007 | Brase et al. |
| 7,288,108 B2 | 10/2007 | DiMauro et al. |
| 7,395,118 B2* | 7/2008 | Erickson ............... A61N 1/05 607/116 |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,684,869 B2 | 3/2010 | Bradley et al. |
| 7,736,382 B2 | 6/2010 | Webb et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,391,985 B2 | 3/2013 | McDonald |
| 8,463,343 B2 | 6/2013 | Kuhn et al. |
| 8,473,061 B2 | 6/2013 | Moffitt et al. |
| 8,483,237 B2 | 7/2013 | Zimmermann et al. |
| 8,571,665 B2 | 10/2013 | Moffitt et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,831,742 B2 | 9/2014 | Pianca et al. |
| 8,849,632 B2 | 9/2014 | Sparks et al. |
| 8,870,857 B2* | 10/2014 | Seymour ............... A61B 5/0084 606/15 |
| 8,936,630 B2 | 1/2015 | Denison et al. |
| 8,958,615 B2 | 2/2015 | Blum et al. |
| 9,415,154 B2 | 8/2016 | Leven |
| 9,550,063 B2 | 1/2017 | Wolf, II |
| 9,681,809 B2* | 6/2017 | Sharma ............... A61B 5/0071 |
| 10,245,441 B2* | 4/2019 | Tischendorf ......... A61N 5/0601 |
| 2002/0156513 A1 | 10/2002 | Borkan |
| 2002/0161417 A1 | 10/2002 | Scribner |
| 2005/0216072 A1 | 9/2005 | Mahadevan-Jansen et al. |
| 2006/0155348 A1 | 7/2006 | deCharms |
| 2006/0161227 A1 | 7/2006 | Walsh, Jr. et al. |
| 2007/0053996 A1 | 3/2007 | Boyden et al. |
| 2007/0150036 A1 | 6/2007 | Anderson |
| 2007/0161919 A1 | 7/2007 | DiLorenzo |
| 2008/0046053 A1 | 2/2008 | Wagner et al. |
| 2008/0077198 A1 | 3/2008 | Webb et al. |
| 2008/0242976 A1* | 10/2008 | Robertson ............ A61B 5/1107 600/425 |
| 2009/0069871 A1 | 3/2009 | Mahadevan-Jansen et al. |
| 2009/0118800 A1 | 5/2009 | Deisseroth et al. |
| 2009/0187222 A1 | 7/2009 | Barker |
| 2009/0276021 A1 | 11/2009 | Meadows et al. |
| 2009/0287272 A1 | 11/2009 | Kokones et al. |
| 2009/0287273 A1 | 11/2009 | Carlton et al. |
| 2010/0076535 A1 | 3/2010 | Pianca et al. |
| 2010/0114190 A1 | 5/2010 | Bendett et al. |
| 2010/0174344 A1 | 7/2010 | Dadd et al. |
| 2010/0268298 A1 | 10/2010 | Moffitt et al. |
| 2010/0292758 A1 | 11/2010 | Lee et al. |
| 2010/0324630 A1 | 12/2010 | Lee et al. |
| 2011/0004267 A1 | 1/2011 | Meadows |
| 2011/0005069 A1 | 1/2011 | Pianca |
| 2011/0046432 A1 | 2/2011 | Simon et al. |
| 2011/0078900 A1 | 4/2011 | Pianca et al. |
| 2011/0125077 A1 | 5/2011 | Denison et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172653 A1 | 7/2011 | Schneider et al. |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0253261 A1 | 10/2012 | Poletto et al. |
| 2012/0314924 A1 | 12/2012 | Carlton et al. |
| 2012/0316615 A1 | 12/2012 | Digiore et al. |
| 2013/0019325 A1 | 1/2013 | Deisseroth et al. |
| 2013/0053905 A1 | 2/2013 | Wagner |
| 2013/0105071 A1 | 5/2013 | Digiore et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0304152 A1 | 11/2013 | Bradley et al. |
| 2013/0317573 A1 | 11/2013 | Zhu et al. |
| 2013/0317575 A1* | 11/2013 | Deisseroth ............ A61N 5/0603 607/92 |
| 2013/0317587 A1 | 11/2013 | Barker |
| 2013/0325091 A1 | 12/2013 | Pianca et al. |
| 2014/0039587 A1 | 2/2014 | Romero |
| 2014/0067023 A1 | 3/2014 | Register et al. |
| 2014/0122379 A1 | 5/2014 | Moffitt et al. |
| 2014/0142664 A1 | 5/2014 | Roukes et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0151113 A1 | 6/2015 | Govea et al. |
| 2015/0306414 A1 | 10/2015 | Nielsen et al. |
| 2015/0375006 A1 | 12/2015 | Denison et al. |
| 2016/0030749 A1 | 2/2016 | Carcieri et al. |
| 2016/0228692 A1 | 8/2016 | Steinke et al. |
| 2016/0271392 A1 | 9/2016 | Vallejo et al. |
| 2016/0346557 A1 | 12/2016 | Bokil |
| 2016/0375258 A1 | 12/2016 | Steinke |
| 2017/0061627 A1 | 3/2017 | Bokil |

(56) References Cited

U.S. PATENT DOCUMENTS

| | | | |
|---|---|---|---|
| 2017/0136254 | A1 | 5/2017 | Simon et al. |
| 2017/0225007 | A1 | 8/2017 | Orinski |
| 2017/0259078 | A1 | 9/2017 | Howard |
| 2017/0304633 | A1 | 10/2017 | Zhang |
| 2018/0064930 | A1 | 3/2018 | Zhang et al. |
| 2018/0078776 | A1 | 3/2018 | Mustakos et al. |
| 2018/0104482 | A1 | 4/2018 | Bokil |
| 2018/0193655 | A1 | 7/2018 | Zhang et al. |
| 2018/0256906 | A1 | 9/2018 | Pivonka et al. |
| 2018/0369606 | A1 | 12/2018 | Zhang et al. |
| 2018/0369607 | A1 | 12/2018 | Zhang et al. |

OTHER PUBLICATIONS

Vivienne L. Tawfik, Su-Youne Chang, Frederick L. Hitti, David W. Roberts, James C. Leiter, Svetlana Jovanovic, Kendall H. Lee, Deep Brain Stimulation Results in Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.

U.S. Appl. No. 16/242,370, filed Jan. 8, 2019, Zhang et al.

U.S. Appl. No. 16/242,461, filed Jan. 8, 2019, Hershey et al.

Baxter, G.D. et al., Effects of Low Intensity Infrared Laser Irradiation Upon Conduction in the Human Median Nerve In Vivo, Experimental Physiology (1994) 79, 227-234.

Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.

Kono, Toru et al., Cord Dorsum Potentials Suppressed by Low Power Laser Irradiation on a Peripheral Nerve in the Cat, Journal of Clinical Laser Medicine & Surgery (1993) 11:3, 115-118.

Snyder-Mackler, Lynn et al., Effect of Helium-Neon Laser Irradiation on Peripheral Sensory Nerve Latency, Phys. Ther. (1988), 68:223-225.

Darlot, Fannie et al., Near-infrared light is neuroprotective in a monkey model of Parkinson's disease (2006), 30 pages.

Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/S0896-6273(00)80955-1.

Barnett L, Platisa J, Popovic M, Pieribone VA, Hughes T. A Fluorescent, Genetically-Encoded Voltage Probe Capable of Resolving Action Potentials, (2012) (http://www.sciencedirect.com/science/article/pii/S0896627300809551).

Brennan KC, Toga AW. Intraoperative Optical Imaging. In: Frostig RD, editor. In Vivo Optical Imaging of Brain Function. 2nd edition. Boca Raton (FL): CRC Press/Taylor & Francis; 2009. Chapter 13. Available from: http://www.ncbi.nlm.nih.gov/books/NBK20224/.

Use of NAD(P)H and flavoprotein autofluorescence transients to probe neuron and astrocyte responses to synaptic activation. Shuttleworth 2010 Neurochemestry international.

* cited by examiner

ELECTRICAL STIMULATION METHODS WITH OPTICAL OBSERVATION AND DEVICES THEREFOR

CROSS-REFERENCE TO RELATED APPLICATIONS

This application claims the benefit under 35 U.S.C. § 119(e) of U.S. Provisional Patent Application Ser. No. 62/411,203, filed Oct. 21, 2016, which is incorporated herein by reference.

FIELD

The present invention is directed to the area of implantable electrical stimulation systems and methods of making and using the systems. The present invention is also directed to implantable electrical stimulation leads having optical elements that facilitate observation and measurement of the effects of electrical stimulation, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a method of monitoring electrical stimulation. The method includes electrically stimulating tissue of the patient using at least one electrode of an implanted electrical stimulation lead. A distal portion of the electrical stimulation lead is disposed adjacent to the tissue of the patient to be stimulated. The electrical stimulation lead includes the at least one electrode and at least one light receiver disposed along the distal portion of the electrical stimulation lead. The method also includes receiving light from the tissue at the at least one light receiver of the lead.

In at least some embodiments, the method further includes implanting the electrical stimulation lead. In at least some embodiments, the method further includes analyzing the received light to monitor the electrical stimulation of the tissue. In at least some embodiments, the method further includes modifying parameters for electrically stimulating the tissue based on the analyzing of the received light. In at least some embodiments, the analyzing and modifying are performed automatically by an implantable control module coupled to the lead.

In at least some embodiments, the method further includes, prior to receiving light from the tissue, emitting light from the at least one light receiver to induce emission of the light from the tissue. In at least some embodiments, the method further includes, prior to receiving light from the tissue, emitting light from at least one light emitter disposed along the distal portion of the electrical stimulation lead to induce emission of the light from the tissue. In at least some embodiments, the received light from the tissue arises from autofluorescence of the tissue.

Another embodiment is a system for monitoring electrical stimulation, the system including an electrical stimulation lead including at least one electrode and at least one light receiver disposed along the distal portion of the electrical stimulation lead. The system also including at least one processor configured to: direct electrical stimulation of tissue of a patient through the at least one electrode of the lead; and analyze light received by the at least one light receiver from the tissue to monitor the electrical stimulation of the tissue. In at least some embodiments, the at least one processor is also configured to modify parameters for electrically stimulating the tissue based on the analyzing of the received light. In at least some embodiments, the at least one processor can also be configured to perform one or more of any other steps of the methods described above.

In at least some embodiments, the system further includes a control module coupleable to the lead, wherein the at least one processor is disposed in the control module. In at least some embodiments, the system further includes a control module coupleable to the lead and a programming unit configured and arranged for communication with the control module, wherein the at least one processor includes a first processor disposed in the control module and a second processor disposed in the programming unit.

Yet another embodiment is a method of monitoring electrical stimulation. The method includes electrically stimulating tissue of the patient using at least one electrode of an implanted electrical stimulation lead. A distal portion of the electrical stimulation lead is disposed adjacent to the tissue of the patient to be stimulated. The electrical stimulation lead includes the at least one electrode and at least one light emitter disposed along the distal portion of the electrical stimulation lead. The method also includes emitting light from the at least one light emitter to induce emission of electrical signals from the tissue; receiving the electrical signals from the tissue at the at least one electrode of the lead; and analyzing the received electrical signals to monitor the electrical stimulation of the tissue.

In at least some embodiments, the method further includes analyzing the received electrical signals to monitor the electrical stimulation of the tissue. In at least some embodiments, the method further includes modifying parameters for electrically stimulating the tissue based on the analyzing of the received electrical signals. In at least some embodiments, the method further includes implanting the electrical stimulation lead.

A further embodiment is a system for monitoring electrical stimulation that includes an electrical stimulation lead including the at least one electrode and at least one light emitter disposed along the distal portion of the electrical stimulation lead. The system also includes at least one processor configured to: direct electrical stimulation of tissue of a patient through the at least one electrode of the lead; direct emission of light from the at least one light emitter to induce emission of electrical signals from the tissue; and analyze electrical signals received by the at least one electrode from the tissue is response to the emission of the light to monitor the electrical stimulation of the tissue. In at least some embodiments, the at least one processor is also configured to modify parameters for electrically stimulating the tissue based on the analyzing of the electrical signals. In at least some embodiments, the at least one processor can also be configured to perform one or more of any other steps of the methods described above.

In at least some embodiments, the system further includes a control module coupleable to the lead, wherein the at least one processor is disposed in the control module. In at least some embodiments, the system further includes a control module coupleable to the lead and a programming unit configured and arranged for communication with the control module, wherein the at least one processor includes a first processor disposed in the control module and a second processor disposed in the programming unit.

Another embodiment is a non-transitory computer-readable medium having processor-executable instructions for monitoring electrical stimulation, the processor-executable instructions when installed onto a device enable the device to perform the any of the methods described above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having optical elements that facilitate observation and measurement of the effects of electrical stimulation, as well as methods of making and using the leads and electrical stimulation systems.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain or spinal cord stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglia stimulation, vagal nerve stimulation, basoreceptor stimulation, or stimulation of other nerves, organs, or tissues.

Figure 1A:
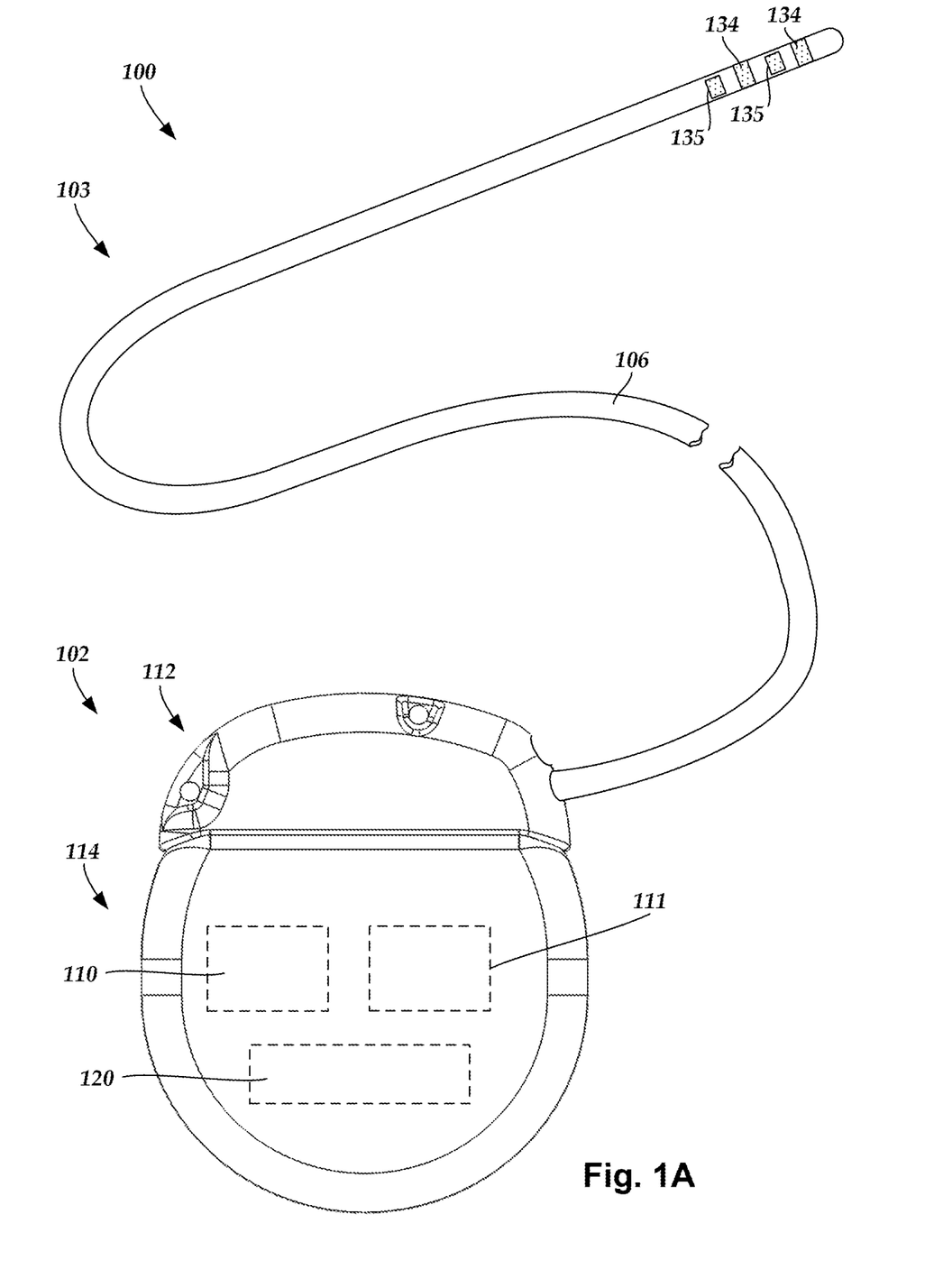
FIG. 1A is a schematic side view of one embodiment of an electrical stimulation system that includes a lead coupled to a control module, according to the invention.
Figure 1B:
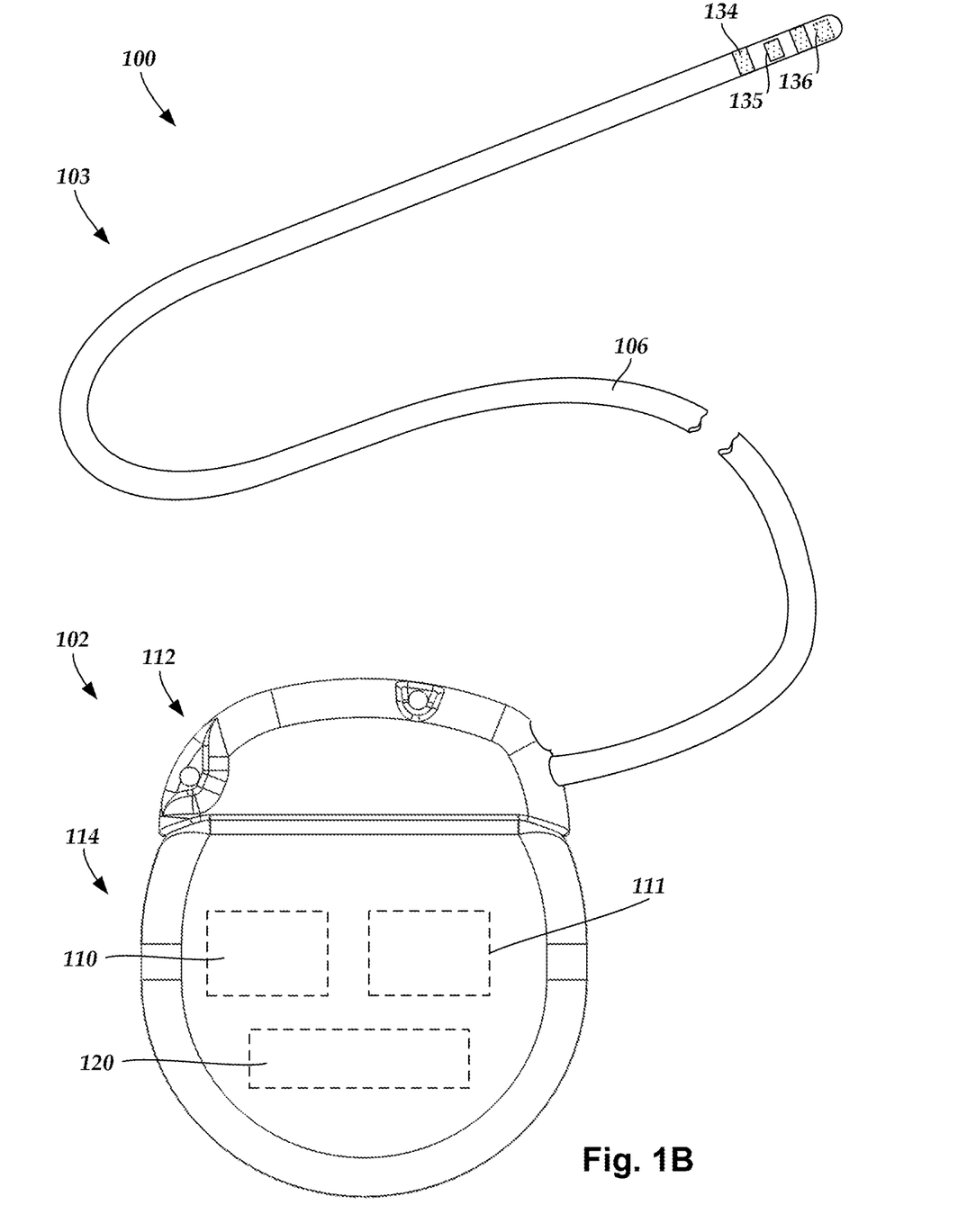
FIG. 1B is a schematic side view of another embodiment of an electrical stimulation system that includes a lead coupled to a control module, according to the invention.
Figure 2A:
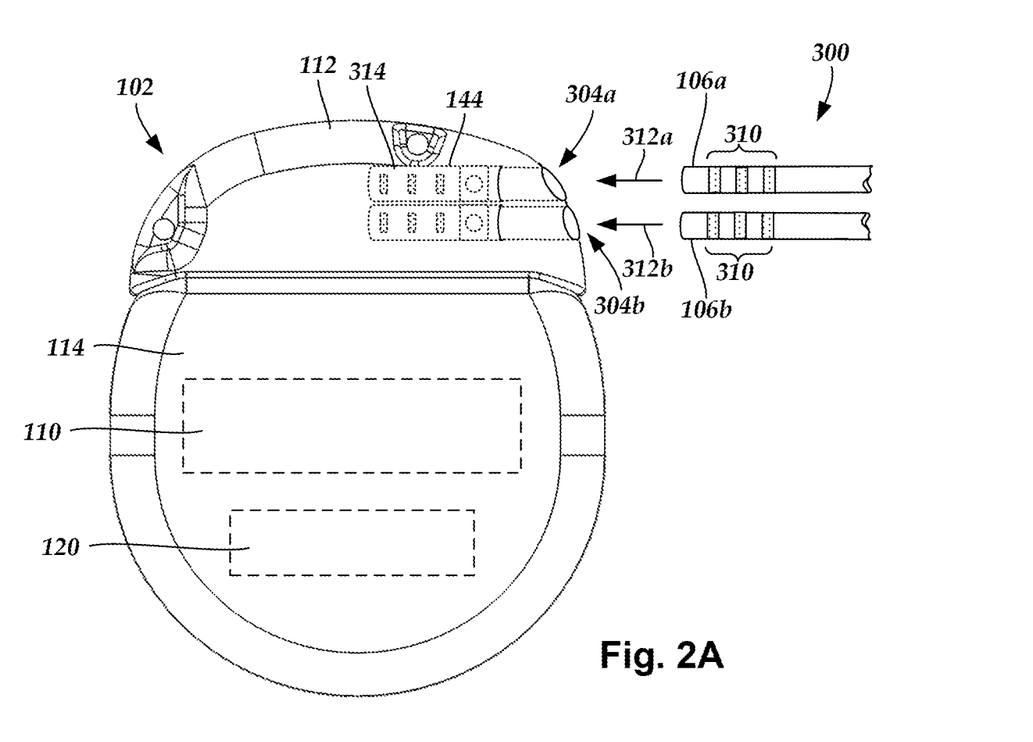
FIG. 2A is a schematic side view of one embodiment of the control module of FIGS. 1A and 1B configured and arranged to couple to an elongated device, according to the invention.

FIGS. 1A and 1B illustrate schematically two embodiments of an electrical stimulation system 100. The electrical stimulation system includes a control module (e.g., a stimulator) 102 and a lead 103 coupleable to the control module 102. The lead 103 includes one or more lead bodies 106. In FIG. 1, the lead 103 is shown having a single lead body 106. In FIG. 2A, the lead includes two lead bodies. It will be understood that the lead 103 can include any suitable number of lead bodies including, for example, one, two, three, four, five, six, seven, eight or more lead bodies 106.

The lead includes one or more electrodes 134 disposed along the lead body 106, and one or more terminals (e.g., 310 in FIG. 2A-2B) disposed along each of the one or more lead bodies 106 and coupled to the electrodes 134 by conductors (not shown). The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 may vary. For example, there can be one, two, four, six, eight, ten, twelve, fourteen, sixteen, or more electrodes 134. As will be recognized, other numbers of electrodes 134 may also be used.

The electrodes 134 can be ring electrodes, tip electrodes, segmented electrodes, or any other suitable type of electrodes or any combination of these types of electrodes. Deep brain stimulation leads and other leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Applications Publication Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. Examples of leads with tip electrodes include at least some of the previously cited references, as well as U.S. Patent Applications Publication Nos. 2014/0296953 and 2014/0343647, all of which are incorporated herein by reference in their entireties.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

At least one light receiver 135 is provided at a distal end of the lead 103, as illustrated in FIG. 1A. In at least some embodiments, the light receiver 135 is also a light emitter. For example, the light receiver 135 can be the end of an optical fiber that extends along the lead and is coupled to a light source (for example, light source 311 of FIG. 3) to deliver light from the light source for emission at the distal end of the lead by the light receiver 135. The light receiver 135 (in this case, the end of the optical fiber) can also receive light from the tissue and transmits the light along the lead to a light sensor (for example, light sensor 388 of FIG. 3). In at least some embodiments, the light receiver 135 only receives light and the lead does not include a light emitter.

In some embodiments, the light receiver 135 can be an element, such as a photodiode, charged coupled device (CCD), or array of photodiodes or CCDs or the like, that receives light and converts the light into an electrical signal and the electrical signals are transmitted along the lead. A light receiver 135 can be selected or tuned to receive light of only a certain wavelength or wavelength range or can be selected to receive light over a broad wavelength range or at multiple wavelengths/ranges. The light can be ultraviolet, visible, or infrared light or any range of wavelengths within these types of light.

In at least some embodiments, the number of light receivers 135 and the number of electrodes 134 is equal with the light receivers and electrodes alternating, as illustrated in FIG. 1A. In other embodiments, the number of light receivers 135 and number of electrodes can be different. For example, for an array of electrodes there may only be one, two (for example, at opposite ends of the array), or three (one at each end and one in the middle) light receivers. In another example, there may be one light receiver for every two electrodes with the light receiver being disposed between the two electrodes. Any other arrangement of light receivers can be used. In embodiments with segmented electrodes, there may be a light receiver for each segmented electrode (with the light receiver oriented in a same direction as the associated segmented electrode) or a single light receiver associated with each circumferential set of segmented electrodes or any other suitable arrangement of light receivers and electrodes.

In some embodiments, there may be one or more light receivers 135 and one or more separate light emitters 136, as illustrated in FIG. 1B. The light emitter can be a terminus of a light transmission element, such as an optical fiber, in which case the light source is distant from the distal end of the light (for example, in the control module or in a proximal portion of the lead or in a lead extension). In other embodiments, the light emitter 136 can be a light source, such as a light emitting diode (LED), laser diode, organic light emitting diode (OLED), or the like, and coupled to the electronic subassembly 110 of the control module to provide signals and power for operating the light source. A light emitter can be selected or tuned to emit light of only a certain wavelength or wavelength range or can be selected to emit light over a broad range. The light can be ultraviolet, visible, or infrared light or any range of wavelengths within these types of light. In some embodiments, there may be multiple light emitters that emit light at different wavelengths or wavelength ranges. Any suitable arrangement and numbers of light receivers, light emitters, and electrodes can be used.

Figure 2B:
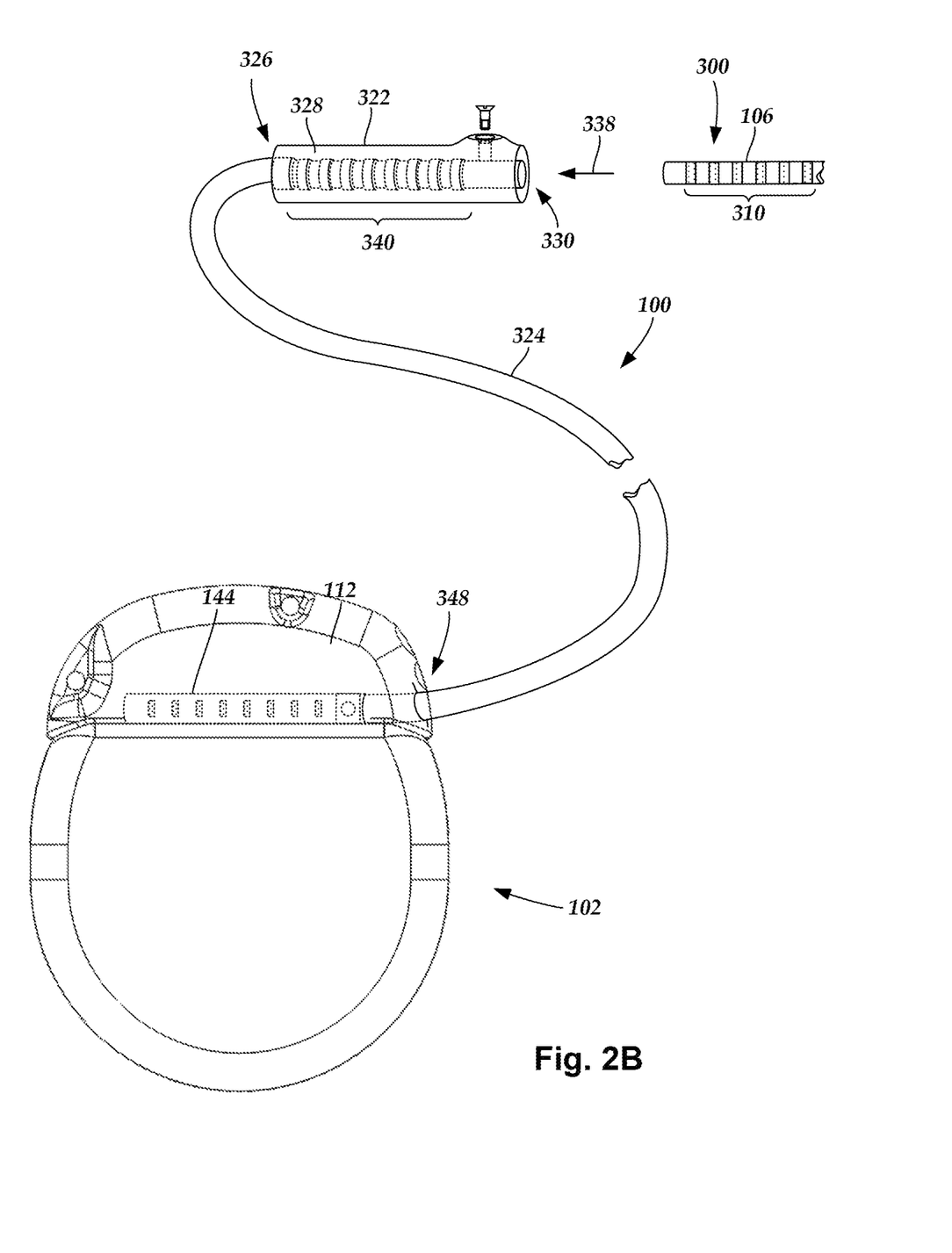
FIG. 2B is a schematic side view of one embodiment of a lead extension configured and arranged to couple the elongated device of FIG. 2A to the control module of FIGS. 1A and 1B, according to the invention.

The lead 103 can be coupled to the control module 102 in any suitable manner. In some embodiments, the lead is permanently attached to the control module 102. In other embodiments, the lead can be coupled to the control module 102 by a connector (e.g., connector 144 of FIG. 2A). In FIG. 2A, the lead 103 is shown coupling directly to the control module 102 through the connector 144. In at least some other embodiments, the lead 103 couples to the control module 102 via one or more intermediate devices, as illustrated in FIG. 2B. For example, in at least some embodiments one or more lead extensions 324 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adapter, or the like or combinations thereof. It will be understood that, in the case where the stimulation system 100 includes multiple elongated devices disposed between the lead 103 and the control module 102, the intermediate devices may be configured into any suitable arrangement.

Returning to FIGS. 1A and 1B, the control module 102 can include, for example, a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

In some embodiments, the control module 102 also includes one or more light sources 111 disposed within the sealed electronics housing 114. The one or more light sources can be, for example, a light emitting diode (LED), laser diode, organic light emitting diode (OLED), or the like. When the control module 102 includes multiple light sources, the light sources can provide light in at a same wavelength or wavelength band or some, or all, of the light sources can provide light at different wavelength or different wavelength bands. When the control module includes one or more light sources 111, the light emitted by the light sources can be directed to an optical fiber (for example, optical fiber) or other light transmitting body for delivery to the light receiver 135. The optical fiber, or a series of optical fibers, can transmit the light from the one or more light sources 111 through the control module 102 and lead 103 to the light receiver 135 (which can be terminus of the optical fiber). In at least some embodiments, the optical fiber is a single mode optical fiber. In other embodiments, the optical fiber is a multi-mode optical fiber. In some embodiments, the system includes a single optical fiber. In other embodiments, the system may employ multiple optical fibers in series or in parallel.

Figure 3:
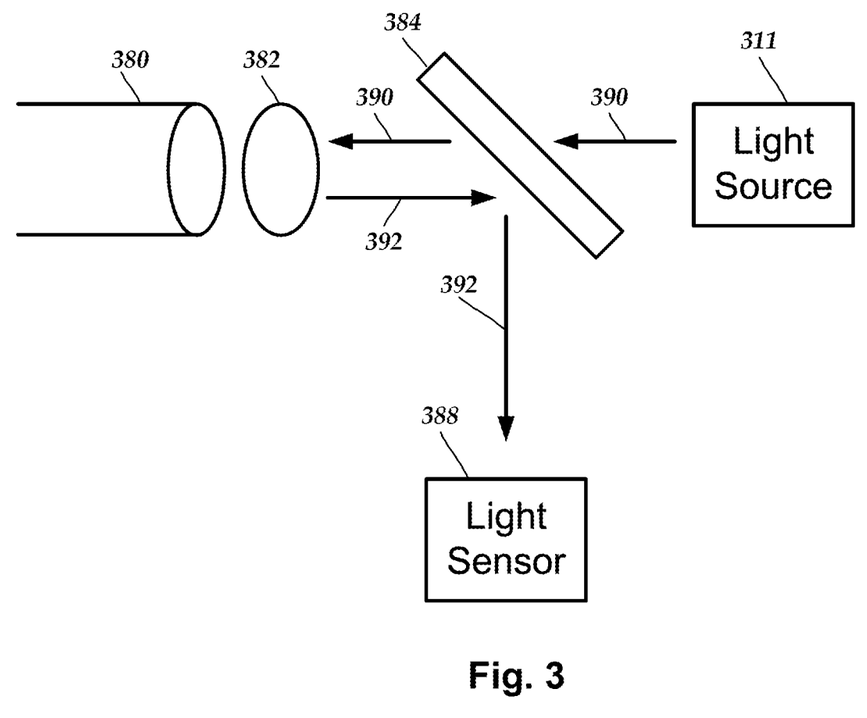
FIG. 3 is a schematic diagram of one embodiment of an optical arrangement for the electrical stimulation systems of FIGS. 1A and 1B, according to the invention.

FIG. 3 illustrates one example of an optical system for producing and detecting light that can be present within the control module (102 in FIG. 1) or elsewhere in the system. The optical system includes a light source 311, an optical fiber 380, a lens 382, a beamsplitter 384, and a light sensor 388. The light source 311 produces light that is directed to the optical fiber 380 through the lens 382 and into the optical fiber 380. The optical fiber 380 is coupled to the lead and a light emitter or light receiver at the end of the lead. When light is received by the light receiver of the lead, that light 392 is transmitted through the lead to the optical fiber 380. through the lens 382, reflected by the beamsplitter 384, and directed to the light sensor 388. Any suitable light sensor can be used including a photodiode, CCD, or an array of photodiodes or CCDs. It will be recognized that other optical arrangements and systems with the same or different components can be used in the control module or elsewhere in the system.

The stimulation system or components of the stimulation system, including the lead 103 and the control module 102, are typically implanted into the body of a patient. The stimulation system can be used for a variety of applications including, but not limited to brain stimulation, deep brain stimulation, neural stimulation, spinal cord stimulation, muscle stimulation, and the like.

Returning to FIGS. 1A-2B, one or more terminals (e.g., 310 in FIGS. 2A-2B) are typically disposed along the proximal end of the one or more lead bodies 106 of the stimulation system 100 (as well as any splitters, lead extensions, adaptors, or the like) for electrical connection to corresponding connector contacts (e.g., 314 in FIGS. 2A-2B). The connector contacts are disposed in connectors (e.g., 144 in FIGS. 1-2B; and 322 FIG. 2B) which, in turn, are disposed on, for example, the control module 102 (or a lead extension, a splitter, an adapter, or the like). Electrically conductive wires, cables, or the like (not shown) extend from the terminals to the light receiver 135 or optional one or more electrodes 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 300 configured and arranged for coupling to one embodiment of the control module connector 144. The one or more elongated devices may include, for example, one or more of the lead bodies 106 of FIGS. 1A and 1B, one or more intermediate devices (e.g., a splitter, the lead extension 324 of FIG. 2B, an adapter, or the like or combinations thereof), or a combination thereof.

The control module connector 144 defines at least one port into which a proximal end of the elongated device 300 can be inserted, as shown by directional arrows 312a and 312b. In FIG. 2A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Each of the terminals 310 can couple to the light receiver 135 or one or more of the optional electrodes 134. Examples of connectors in control modules are found in, for example, U.S. Pat. Nos. 7,244,150 and 8,224,450, which are incorporated by reference.

FIG. 2B is a schematic side view of another embodiment of the stimulation system 100. The stimulation system 100 includes a lead extension 324 that is configured and arranged to couple one or more elongated devices 300 (e.g., one of the lead bodies 106 of FIG. 1, a splitter, an adapter, another lead extension, or the like or combinations thereof) to the control module 102. In FIG. 2B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144 (e.g., the ports 304*a* and 304*b* of FIG. 1), or to receive multiple elongated devices 300 (e.g., both of the lead bodies 106 of FIG. 1), or both.

A lead extension connector 322 is disposed on the lead extension 324. In FIG. 2B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. Each of the terminals 310 can couple to the light receiver 135 or one or more of the optional electrodes 134. The connector housing 328 also includes a plurality of connector contacts, such as connector contact 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIG. 1) disposed along the lead (103 in FIG. 1).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 2B), the proximal end 348 of the lead extension 324 is configured and arranged for insertion into the control module connector 144.

It is useful for a clinician or user to determine the effect of electrical stimulation using a lead and control module. In some conventional systems, the effects are reported by the patient, observed by the clinician, or measured using one or more external sensors.

Figure 4A:
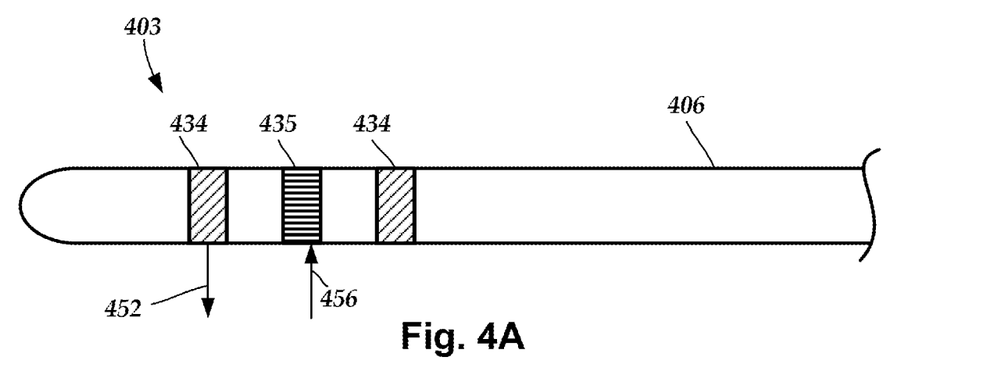
FIG. 4A is a schematic cross-sectional view of one embodiment of an electrical stimulation lead and a method of optically monitoring the electrical stimulation, according to the invention.
Figure 4B:
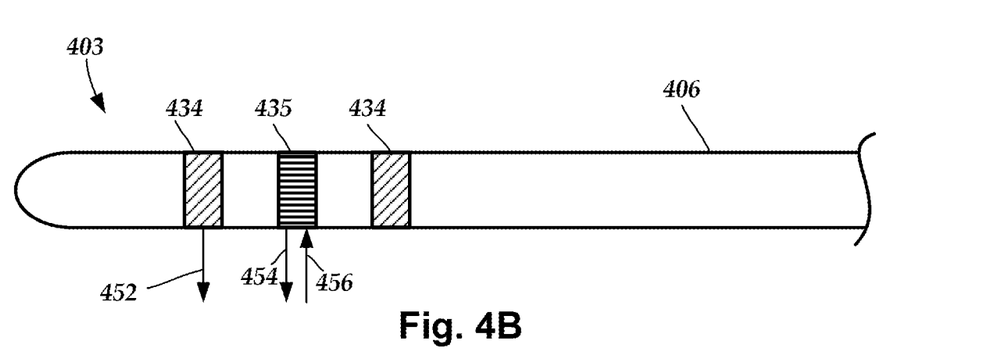
FIG. 4B is a schematic cross-sectional view of one embodiment of an electrical stimulation lead and another method of optically monitoring the electrical stimulation, according to the invention.
Figure 4C:
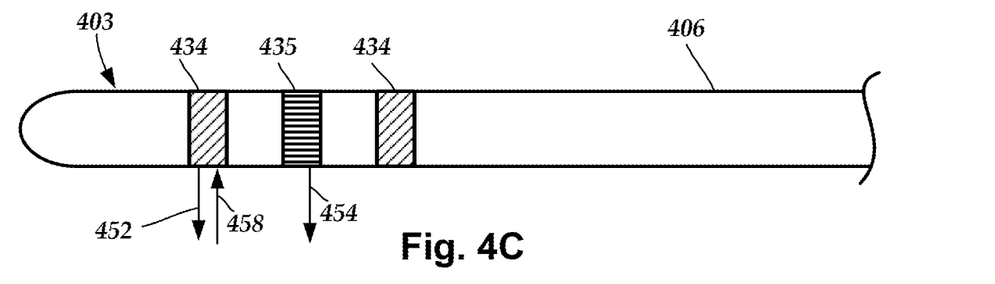
FIG. 4C is a schematic cross-sectional view of one embodiment of an electrical stimulation lead and a method of optically/electrically monitoring the electrical stimulation, according to the invention.

As described herein, however, the light receiver and optional light emitter on a lead can be used to probe or otherwise observe the effects of electrical stimulation conveyed through the electrodes of the lead. FIGS. 4A-4C illustrate examples of different methods of observation of the effects of electrical stimulation. FIGS. 4A-4C illustrate a lead 403 with a lead body 406, one or more electrodes 434, and at least one light receiver 435. It will be understood that, as discussed above, the light receiver 435 may also act as a light emitter in some embodiments or that the lead 403 may include a separate light emitter.

In some embodiments, the light receiver is arranged to receive light generated by tissue as part of the function of the tissue or in response to electrical stimulation or any combination thereof. For example, at least some neural tissues, or molecules or components within the neural tissues, produce autofluorescence during normal or abnormal functioning, for example, as a consequence of changes in metabolism. Examples of autofluorescing molecules or other tissue components include, but are not limited to, NAD(P)H and flavoprotein. The light receiver can receive the light from this autofluorescence and convey that light (or electrical signals generated in the light receiver by that light) to the control module for monitoring or analysis.

FIG. 4A illustrates one embodiment in which electrical stimulation 452 is provided through one or more of the electrodes 452 of the lead 403. In response to the electrical stimulation, light 456 is generated and received by the at least one light receiver 435. In some embodiments, the light 456 may also be generated prior to stimulation and the arrangement monitors or measures changes in the light such as, for example, changes in intensity, frequency, or the like. The received light 456 can be used to monitor, observe, or measure the results of electrical stimulation 452.

Figure 6:
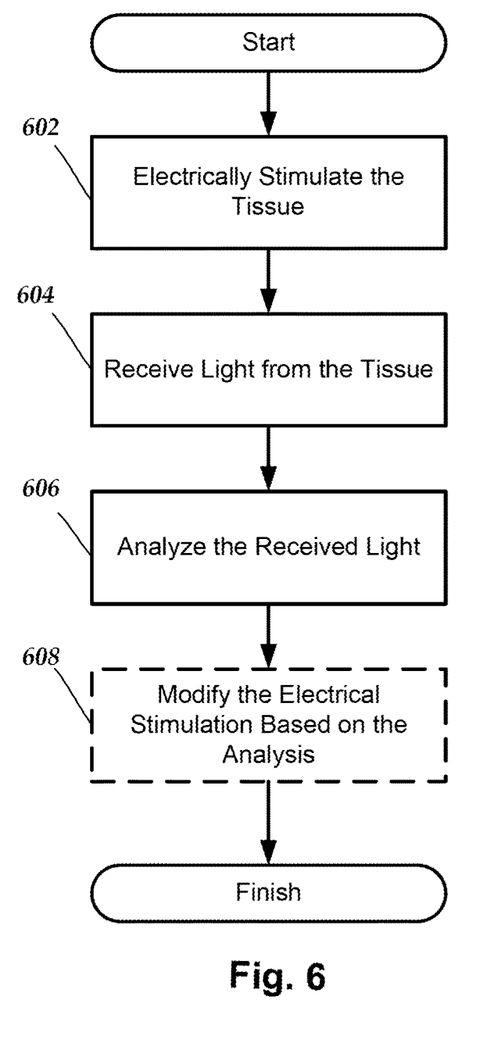
FIG. 6 is a flowchart of one method of monitoring electrical stimulation, according to the invention.

FIG. 6 illustrates one embodiment of steps of method for monitoring electrical stimulation. In step 602, the tissue is electrically stimulated by the electrodes of the lead. In step 604, light is received from the tissue by the light receiver. In step 606, the received light is analyzed. In step 608, optionally, parameters of the electrical stimulation are modified based on the analysis of the received light.

In other embodiments, light may be emitted by the light receiver or light emitter and an optical response to the emitted light by the tissue may be observed using the light receiver. For example, light may be utilized to induce fluorescence or produce second or higher order harmonic emissions or otherwise cause the emission of light by neural tissue (or molecules or other components within in the neural tissue.) The emitted light can be used to probe the neural tissue before, during, or after stimulation and used to measure or monitor the effects of stimulation.

FIG. 4B illustrates one embodiment in which electrical stimulation 452 is provided through one or more of the electrodes 452. Light 454 is emitted by the light receiver 435 (or a separate light emitter) to probe the tissue. In response to the electrical stimulation 452 and the emitted light 454, light 456 is generated by the tissue and received by the at least one light receiver 435. In some embodiments, the light 456 may also be generated by the tissue prior to electrical stimulation (and, optionally, after emission of light 454 from the lead) and the arrangement monitors or measures changes in the light 456 such as, for example, changes in intensity, frequency, or the like. The received light 456 can be used to monitor, observe, or measure the results of electrical stimulation 452.

Figure 7:
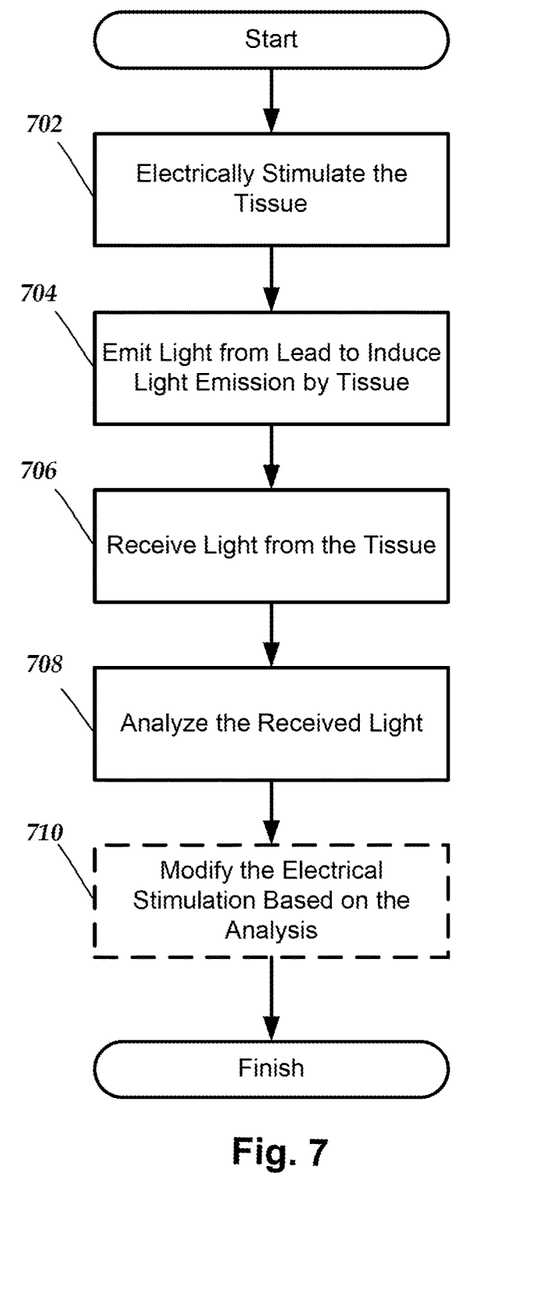
FIG. 7 is a flowchart of another method of monitoring electrical stimulation, according to the invention.

FIG. 7 illustrates one embodiment of steps of method for monitoring electrical stimulation. In step 702, the tissue is electrically stimulated by the electrodes of the lead. In step 704, light is emitted from the lead to induce light emission by the tissue. In step 706, light is received from the tissue by the light receiver. In step 708, the received light is analyzed. In step 710, optionally, parameters of the electrical stimulation are modified based on the analysis of the received light. In at least some embodiments, steps 702-706 can be performed simultaneously to simultaneously stimulate and illuminate the tissue to detect fluorescence changes.

In yet other embodiments, light may be emitted by the light receiver or light emitter and an electrical response by tissue to the emitted light may be obtained using one or more of the electrodes. For example, light may be utilized to induce an electrical response in neural tissue (or molecules or other components within in the neural tissue.) The emitted light can be used to probe the neural tissue before, during, or after stimulation and used to measure or monitor the effects of stimulation.

FIG. 4C illustrates one embodiment in which electrical stimulation 452 is provided through one or more of the electrodes 452. Light 454 is emitted by the light receiver 435 (or a separate light emitter) to probe the tissue. In response to the electrical stimulation 452 and the emitted light 454, electrical signals 458 are generated by the tissue and received by one or more of the electrodes 434. In some embodiments, the electrical signals 458 may also be generated by tissue prior to electrical stimulation (and, optionally, after emission of light 454 from the lead) and the arrangement monitors or measures changes in the electrical signals 458 such as, for example, changes in intensity, frequency, or the like. The light-induced electrical signal 458 can be used to monitor, observe, or measure the results of electrical stimulation 452.

Figure 8:
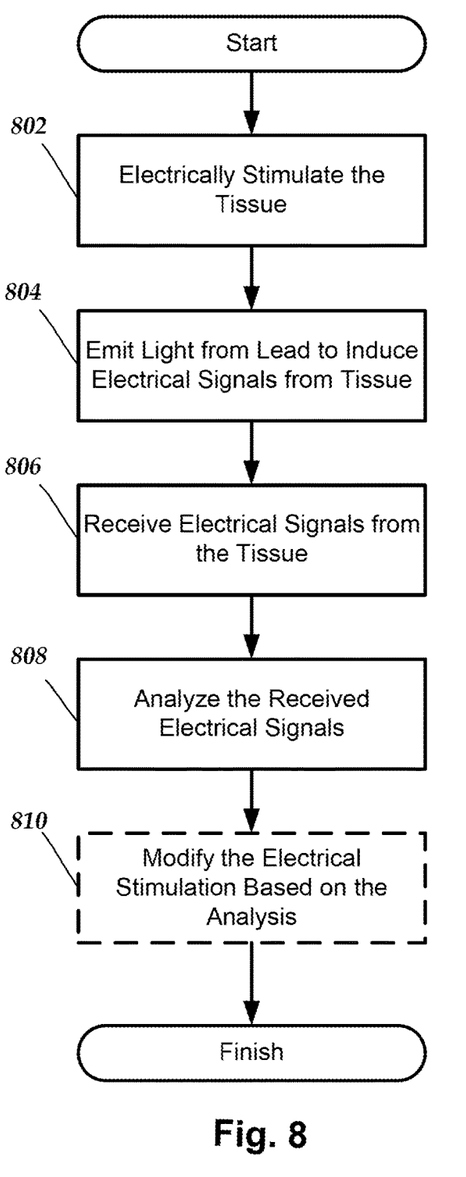
FIG. 8 is a flowchart of a third method of monitoring electrical stimulation, according to the invention.

FIG. 8 illustrates one embodiment of steps of method for monitoring electrical stimulation. In step 802, the tissue is electrically stimulated by the electrodes of the lead. In step 804, light is emitted from the lead to induce electrical signals from the tissue. In step 806, electrical signals are received from the tissue by the one or more electrodes. In step 808, the received electrical signals are analyzed. In step 810, optionally, parameters of the electrical stimulation are modified based on the analysis of the received electrical signals.

Figure 4D:
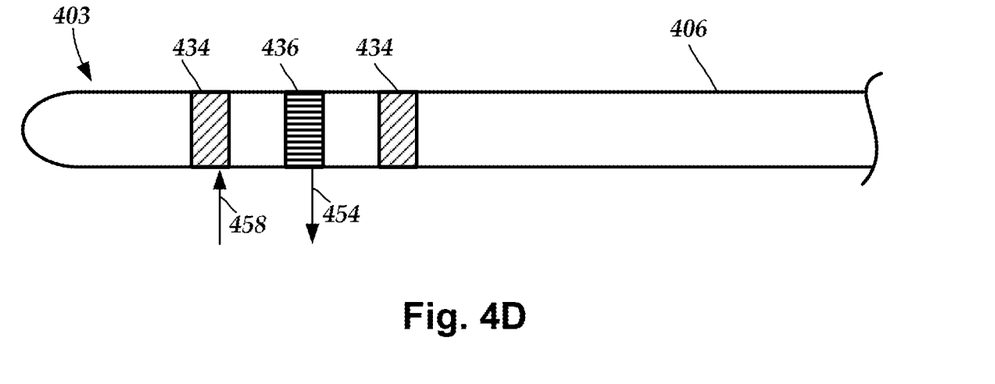
FIG. 4D is a schematic cross-sectional view of one embodiment of an optical stimulation lead and a method of electrically monitoring the electrical stimulation, according to the invention.

FIG. 4D illustrates an example of electrical observation of the effects of optical stimulation. Light 454 is emitted by the light emitter 436 to stimulate the tissue. In response to the optical stimulation 454, electrical signals 458 are generated by the tissue and received by one or more of the electrodes 434. In some embodiments, the electrical signals 458 may also be generated by tissue prior to optical stimulation and the arrangement monitors or measures changes in the electrical signals 458 such as, for example, changes in intensity, frequency, or the like.

Figure 9:
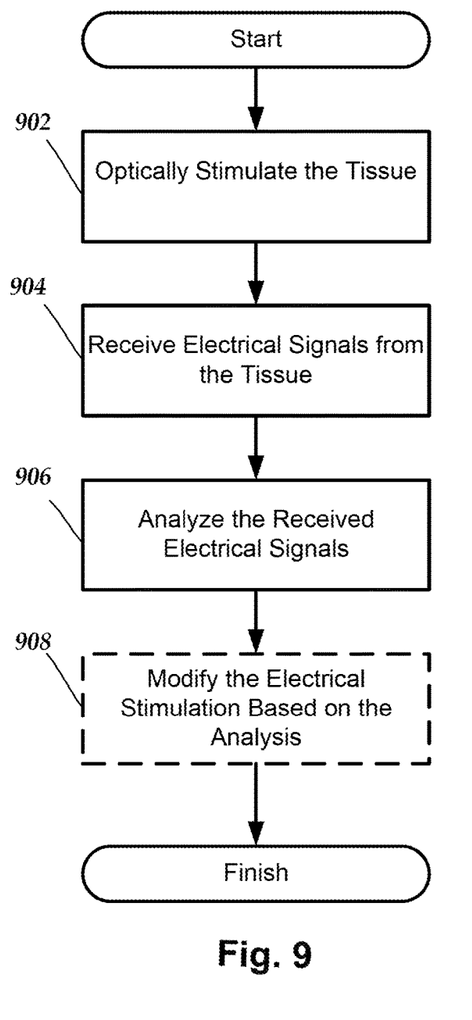
FIG. 9 is a flowchart of one method of monitoring optical stimulation, according to the invention.

FIG. 9 illustrates one embodiment of steps of method for monitoring electrical stimulation. In step 902, the tissue is optically stimulated by the lead. In step 904, electrical signals are received from the tissue by the one or more electrodes. In step 906, the received electrical signals are analyzed. In step 908, optionally, parameters of the electrical stimulation are modified based on the analysis of the received electrical signals.

In at least some embodiments, the observation of electrical or optical stimulation described above with respect to FIGS. 4A-4D and 6-9 may be user-controlled or user-directed. For example, such observation may only be performed if directed by the user, such as a clinician, patient, programmer, or other individual. In other embodiments, the observation may be automatic, without user direction or control, or may be automatic in response to a user direction to initiate automatic observation. The observation may be continuous, periodic, or performed at random times or intervals, or any combination thereof.

In some embodiments, the observed light or electrical signals are provided to sensor (for example, light sensor 388 in FIG. 3 or another optical or electrical sensor) and the data generated by the sensor can be stored or evaluated on the control module. Alternatively or additionally, the sensor data may be transmitted or otherwise delivered to an external device, such as a programming device (for example, programming unit 508 of FIG. 5). In at least some embodiments, a user may be allowed to observe the sensor data and alter stimulation parameters.

In some embodiments, the data generated by the sensor may be observed or evaluated by the control module (or an external device) and used to automatically modify one or more stimulation parameters. In this manner, the observation of the effects of the electrical or optical stimulation can act in a closed-loop feedback system, including at least the lead and control module, to monitor and modify the stimulation based on the observed effect.

In addition, in some embodiments, the observation of the effect of stimulation may also be used to facilitate placement of the lead. For example, the lead may be positioned in tissue, the tissue is then stimulated, and the observation of the stimulation, as described above, can facilitate whether the position of the lead is acceptable or whether the lead should be repositioned.

Figure 5:
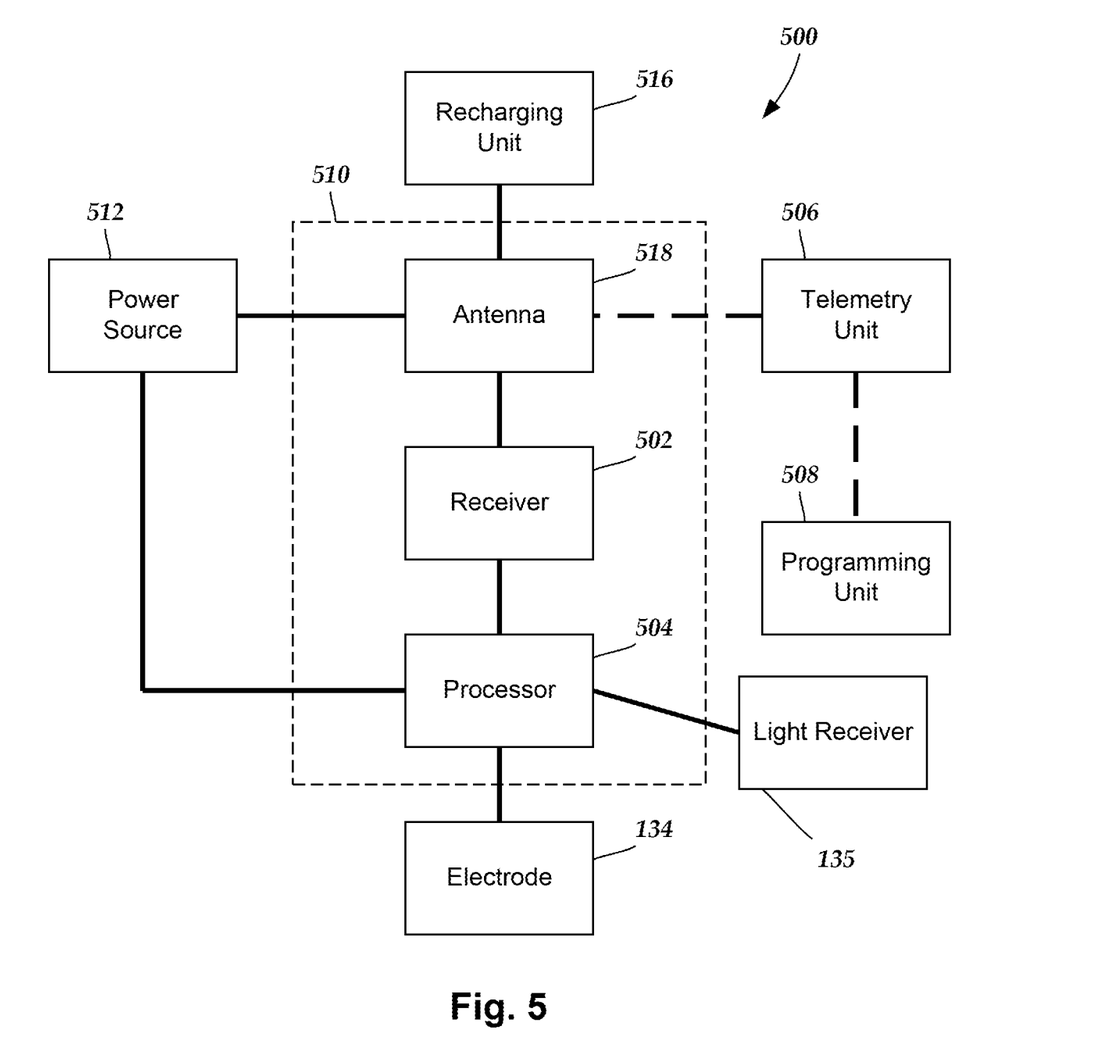
FIG. 5 is a schematic overview of one embodiment of components of a stimulation system, including an electronic subassembly disposed within a control module, according to the invention.

FIG. 5 is a schematic overview of one embodiment of components of an electrical stimulation system 500 including an electronic subassembly 510 disposed within a control module. It will be understood that the electrical stimulation system can include more, fewer, or different components and can have a variety of different configurations including those configurations disclosed in the stimulator references cited herein.

Some of the components (for example, a power source 512, an antenna 518, a receiver 502, and a processor 504) of the electrical stimulation system can be positioned on one or more circuit boards or similar carriers within a sealed housing of an implantable pulse generator, if desired. Any power source 512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 5,437,193, incorporated herein by reference.

As another alternative, power can be supplied by an external power source through inductive coupling via the optional antenna 518 or a secondary antenna. The external power source can be in a device that is mounted on the skin of the user or in a unit that is provided near the user on a permanent or periodic basis.

If the power source 512 is a rechargeable battery, the battery may be recharged using the optional antenna 518, if desired. Power can be provided to the battery for recharging by inductively coupling the battery through the antenna to a recharging unit 516 external to the user. Examples of such arrangements can be found in the references identified above.

In at least some embodiments, electrical signals are delivered through the electrodes 134 of the lead body to stimulate nerve fibers, muscle fibers, or other body tissues near the electrical stimulation system. Light from the tissue can be received by the light receiver 135 and delivered to the processor 504. The processor 504 is generally included to control the timing and other characteristics of the electrical stimulation system. For example, the processor 504 can, if desired, control one or more of the timing, pulse frequency, strength, duration, and waveform of the electrical stimulation. In some embodiments, the processor 504 selects which of the electrode(s) are cathodes and which electrode(s) are anodes. In addition, the processor 504 may receive and evaluate or store signals from the light receiver or a sensor coupled to the light receiver, if desired.

Any processor can be used and can be as simple as an electronic device that, for example, produces electrical stimulation at a regular interval or the processor can be capable of receiving and interpreting instructions from an external programming unit 508 that, for example, allows modification of stimulation characteristics. In the illustrated embodiment, the processor 504 is coupled to a receiver 502 which, in turn, is coupled to the optional antenna 518. This allows the processor 504 to receive instructions from an external source to, for example, direct the stimulation characteristics and the selection of electrodes, if desired.

In one embodiment, the antenna 518 is capable of receiving signals (e.g., RF signals) from an external telemetry unit 506 which is programmed by the programming unit 508. The programming unit 508 can be external to, or part of, the telemetry unit 506. The telemetry unit 506 can be a device that is worn on the skin of the user or can be carried by the user and can have a form similar to a pager, cellular phone, or remote control, if desired. As another alternative, the telemetry unit 506 may not be worn or carried by the user but may only be available at a home station or at a clinician's office. The programming unit 508 can be any unit that can provide information to the telemetry unit 506 for transmission to the electrical stimulation system 500. The programming unit 508 can be part of the telemetry unit 506 or can provide signals or information to the telemetry unit 506 via a wireless or wired connection. One example of a suitable programming unit is a computer operated by the user or clinician to send signals to the telemetry unit 506.

The signals sent to the processor 504 via the antenna 518 and the receiver 502 can be used to modify or otherwise direct the operation of the electrical stimulation system. For example, the signals may be used to modify the stimulation characteristics of the electrical stimulation system such as modifying one or more of stimulation duration, pulse frequency, waveform, and stimulation amplitude. The signals may also direct the electrical stimulation system 500 to cease operation, to start operation, to start charging the battery, or to stop charging the battery. In other embodiments, the stimulation system does not include the antenna 518 or receiver 502 and the processor 504 operates as programmed.

Optionally, the electrical stimulation system 500 may include a transmitter (not shown) coupled to the processor 504 and the antenna 518 for transmitting signals back to the telemetry unit 506 or another unit capable of receiving the signals. For example, the electrical stimulation system 500 may transmit signals indicating whether the electrical stimulation system 500 is operating properly or not or indicating when the battery needs to be charged or the level of charge remaining in the battery. The processor 504 may also be capable of transmitting information about the stimulation characteristics so that a user or clinician can determine or verify the characteristics.

The methods of monitoring electrical or optical stimulation (such as those described with respect to FIGS. 6-9) can be performed fully or at least partially with the processor 504 of the control module. Additionally or alternatively, some or all of the steps may be performed using a processor external to the control module such as, for example, a processor in the programming unit 508.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A method of monitoring electrical stimulation of a patient, the method comprising:

electrically stimulating neural tissue of the patient using at least one electrode of an implanted electrical stimulation lead to induce autofluorescence of the neural tissue, wherein a distal portion of the electrical stimulation lead is disposed adjacent to the neural tissue of the patient to be stimulated, the electrical stimulation lead comprising the at least one electrode and at least one light receiver disposed along a distal portion of the electrical stimulation lead; and receiving light from the autofluorescence of the neural tissue at the at least one light receiver of the electrical stimulation lead.

2. The method of claim 1, further comprising implanting the electrical stimulation lead.

3. The method of claim 1, further comprising analyzing the received light to monitor the electrical stimulation of the neural tissue.

4. The method of claim 3, further comprising modifying parameters for electrically stimulating the neural tissue based on the analyzing of the received light.

5. The method of claim 4, wherein the analyzing and modifying are performed automatically by an implantable control module coupled to the electrical stimulation lead.

6. The method of claim 1, further comprising, prior to receiving light from the neural tissue, emitting light from the at least one light receiver to induce emission of the light from the autofluorescence of the neural tissue.

7. The method of claim 1, further comprising, prior to receiving light from the neural tissue, emitting light from at least one light emitter disposed along the distal portion of the electrical stimulation lead to induce emission of the light from the autofluorescence of the neural tissue.

8. A non-transitory computer-readable medium having processor-executable instructions for monitoring electrical stimulation, the processor-executable instructions when installed onto a device enable the device to perform the method of claim 1.

9. The method of claim 1, wherein electrically stimulating neural tissue comprises electrically stimulating neural tissue to induce autofluorescence of NAD(P)H or flavoprotein, wherein receiving light comprise receiving light from the autofluorescence of the NAD(P)H or flavoprotein.

10. A system for monitoring electrical stimulation, the system comprising:
    an electrical stimulation lead comprising at least one electrode and at least one light receiver disposed along a distal portion of the electrical stimulation lead; and
    at least one processor configured to:
        direct electrical stimulation of neural tissue of a patient through the at least one electrode of the electrical stimulation lead to induce autofluorescence of the neural tissue;
        analyze light received by the at least one light receiver from the autofluorescence of the neural tissue to monitor the electrical stimulation of the neural tissue; and
        modify parameters for electrically stimulating the neural tissue based on the analyzing of the received light.

11. The system of claim 10, further comprising a control module coupleable to the electrical stimulation lead, wherein the at least one processor is disposed in the control module.

12. The system of claim 10, further comprising a control module coupleable to the electrical stimulation lead and a programming unit configured and arranged for communication with the control module, wherein the at least one processor comprises a first processor disposed in the control module and a second processor disposed in the programming unit.

13. A method of monitoring electrical stimulation, the method comprising:
    electrically stimulating tissue of a patient using at least one electrode of an implanted electrical stimulation lead, wherein a distal portion of the electrical stimulation lead is disposed adjacent to the tissue of the patient to be stimulated, the electrical stimulation lead comprising the at least one electrode and at least one light emitter disposed along the distal portion of the electrical stimulation lead; and
    emitting light from the at least one light emitter to probe the electrically stimulated tissue and to induce emission of electrical signals from the electrically stimulated tissue;
    receiving the electrical signals from the electrically stimulated tissue at the at least one electrode of the lead; and
    analyzing the received electrical signals to monitor the electrical stimulation of the electrically stimulated tissue.

14. The method of claim 13, further comprising analyzing the received electrical signals to monitor the electrical stimulation of the electrically stimulated tissue.

15. The method of claim 14, further comprising modifying parameters for electrically stimulating the tissue based on the analyzing of the received electrical signals.

16. The method of claim 13, further comprising implanting the electrical stimulation lead.

17. A non-transitory computer-readable medium having processor-executable instructions for monitoring electrical stimulation, the processor-executable instructions when installed onto a device enable the device to perform the method of claim 13.

18. A system for monitoring electrical stimulation, the system comprising:
    an electrical stimulation lead comprising at least one electrode and at least one light emitter disposed along a distal portion of electrical stimulation lead; and
    at least one processor configured to perform the method of claim 13.

19. The system of claim 18, further comprising a control module coupleable to the electrical stimulation lead, wherein the at least one processor is disposed in the control module.

20. The system of claim 18, further comprising a control module coupleable to the electrical stimulation lead and a programming unit configured and arranged for communication with the control module, wherein the at least one processor comprises a first processor disposed in the control module and a second processor disposed in the programming unit.

* * * * *